(12) United States Patent
Kim et al.

(10) Patent No.: US 7,856,322 B2
(45) Date of Patent: Dec. 21, 2010

(54) METHOD AND APPARATUS FOR DETERMINING SPECIFICITY OF A CANDIDATE PROBE

(75) Inventors: Ki-eun Kim, Seoul (KR); Ji-young Oh, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 622 days.

(21) Appl. No.: 11/610,185

(22) Filed: Dec. 13, 2006

(65) Prior Publication Data

US 2007/0225920 A1 Sep. 27, 2007

(30) Foreign Application Priority Data

Mar. 21, 2006 (KR) .................. 10-2006-0025672

(51) Int. Cl.
*G06F 7/00* (2006.01)

(52) U.S. Cl. ............... 702/19; 702/20; 703/11; 435/6; 435/7.1; 536/24.5

(58) Field of Classification Search ............... None
See application file for complete search history.

(56) References Cited

U.S. PATENT DOCUMENTS 6,312,903 B1* 11/2001 Jannes et al. .................. 435/6
7,065,451 B2* 6/2006 Garner et al. ................ 702/20

FOREIGN PATENT DOCUMENTS

KR 1020050009052 1/2005

* cited by examiner

*Primary Examiner*—Mary K Zeman
(74) *Attorney, Agent, or Firm*—Cantor Colburn LLP

(57) ABSTRACT

Provided are a method and apparatus for determining specificity of a candidate probe.

15 Claims, 5 Drawing Sheets

FIG. 2

| Ranks: | higher taxa | genus | species | lower taxa | tatal |
|---|---|---|---|---|---|
| Archaea | 85 | 90 | 521 | 41 | 737 |
| Bacteria | 845 | 1502 | 19928 | 2228 | 24503 |
| Eukaryota | 12779 | 35264 | 120414 | 8396 | 176853 |
| Fungi | 910 | 2769 | 14442 | 746 | 18867 |
| Metazoa | 9202 | 20051 | 51058 | 4372 | 84683 |
| Viridiplantae | 1738 | 10803 | 50056 | 2936 | 65533 |
| Viruses | 367 | 267 | 3839 | 13081 | 17554 |
| all taxa | 14093 | 37130 | 147747 | 23771 | 22741 | though

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: candidate probe
<220> FEATURE:
<221> NAME/KEY: misc_feature
<222> LOCATION: (18)..(18)
<223> OTHER INFORMATION: n is a, c, g, or t

<400> SEQUENCE: 1
aacttyatgt ccatgggngc                                              20

<210> SEQ ID NO 2
<211> LENGTH: 20
<212> TYPE: DNA
<213> ORGANISM: Artificial Sequence
<220> FEATURE:
<223> OTHER INFORMATION: candidate probe

<400> SEQUENCE: 2
cagccagctg agccaattca                                              20
```

METHOD AND APPARATUS FOR DETERMINING SPECIFICITY OF A CANDIDATE PROBE

This application claims priority to Korean Patent Application No. 10-2006-0025672, filed on Mar. 21, 2006, in the Korean Intellectual Property Office, incorporated herein in its entirety by reference.

BACKGROUND OF THE INVENTION

1. Field of the Invention

The present invention relates to a method and apparatus for determining the specificity of a candidate probe sequence.

2. Description of the Related Art

The interest in microarrays using oligonucleotides has greatly increased because a small number of experiments performed with such devices can produce a large amount of biological information. A microarray immobilizes oligonucleotides on a substrate which can function as probes. The probes on the microarray can then hybridize to a nucleic acid from which biological information is to be obtained, and the degree of hybridization can be measured, thereby obtaining biological information. Such microarrays can be applied in identifying gene expression, identifying specific gene information of a genome, and detecting pathogens.

One of the most important processes for preparing a microarray is the selection of an effective probe. In general, a suitable probe can be selected by predetermining the hybridization strength between a nucleic acid in a sample and the potential probe to be hybridized thereto. However, because information on nucleic acid sequences is not known for all species and some species exist which have similar nucleic acid sequences, selecting a probe is not always a simple process.

For example, when detecting pathogens in a sample, even if the presence of one kind of pathogen is detected and identified, different kinds of pathogens may actually coexist in the sample. In particular, multiple pathogens may coexist in applications such as predicting diseases or detecting food poisoning bacteria. Therefore, selecting a probe which hybridizes specifically with a particular pathogen, or class of pathogens, and hybridizes non-specifically to other pathogens is important for such applications.

Although these concerns are considered mainly in the initial stage of designing a probe, designing a probe using all known genes of bacteria or other pathogens is impossible and inefficient. However, if there is no consideration as to whether a candidate probe will simultaneously detect a target pathogen as well as other non-target pathogens, a large number of experimental errors may occur. Accordingly, a prior art process of designing a probe involves first designing the probe to hybridize with a limited number of major pathogens, and then experimentally determining whether the major pathogens are detected by the probe in samples.

Although such a probe selecting method including experimental detection can easily yield a probe that can hybridize to a target pathogen, using such a method to select a probe which is specific for the target pathogen, but non-specific for related pathogens is difficult, and requires an increase in time and cost in selecting the probe.

Factors that must be considered in designing a probe have changed, and their number has increased. For example, gene sequences are being updated on a daily basis, new species of bacteria and other pathogens are being found, and the taxonomic classification system of species is changing. Also, gene expression information and phylogenetic trees for species are being updated. Therefore, if a probe prepared one year ago is used this year, the validity of the specificity of the probe may not be guaranteed. Consequently, there is a need to check the specificity of previously designed probes or microarrays.

BRIEF SUMMARY OF THE INVENTION

The present invention provides a method for determining specificity of a candidate probe sequence.

In one embodiment, the method comprises: extracting a gene sequence from a gene sequence database, wherein the gene sequence database comprises gene sequence related information, wherein the extracted gene sequence comprises a sequence homologous with a candidate probe sequence; identifying a name of a species corresponding to the extracted gene sequence using a taxonomy database, wherein the taxonomy database comprises biological taxonomic information and gene sequence information; outputting the name of the species of the extracted gene; outputting a name for each species included in a biological taxonomic category not homologous to the candidate probe sequence; and evaluating a degree of homology between the extracted gene sequence and the candidate probe sequence.

The present invention also provides an apparatus for determining specificity of a candidate probe sequence.

In one embodiment, the apparatus comprises: a gene sequence extracting unit, for extracting a gene sequence from a gene sequence database, wherein the extracted gene sequence comprises a sequence with homology to a sequence of a candidate probe; a species name indexing unit, for indexing a name of a species corresponding to the extracted gene sequence using information regarding the extracted gene sequence extracted from a taxonomy database; a species name extracting unit, for extracting a name of a species to be detected by the candidate probe sequence from the indexed names of species, and names of species included in a biological taxonomic category not to be detected by the candidate probe sequence from the names of species indexed using a phylogenetic tree database; and a homology evaluating unit, for evaluating a homology between the sequence with homology to the sequence of a candidate probe contained in the extracted gene sequence and the sequence of the candidate probe.

BRIEF DESCRIPTION OF THE DRAWINGS

The above and other features and advantages of the present invention will become more apparent by describing in detail exemplary embodiments thereof with reference to the attached drawings in which:

FIG. 2 is a table illustrating the contents of an exemplary embodiment of a taxonomy database according to the present invention;

DETAILED DESCRIPTION OF THE INVENTION

Hereinafter, the present invention will be described more fully with reference to the accompanying drawings, in which exemplary embodiments of the invention are shown.

Figure 1:
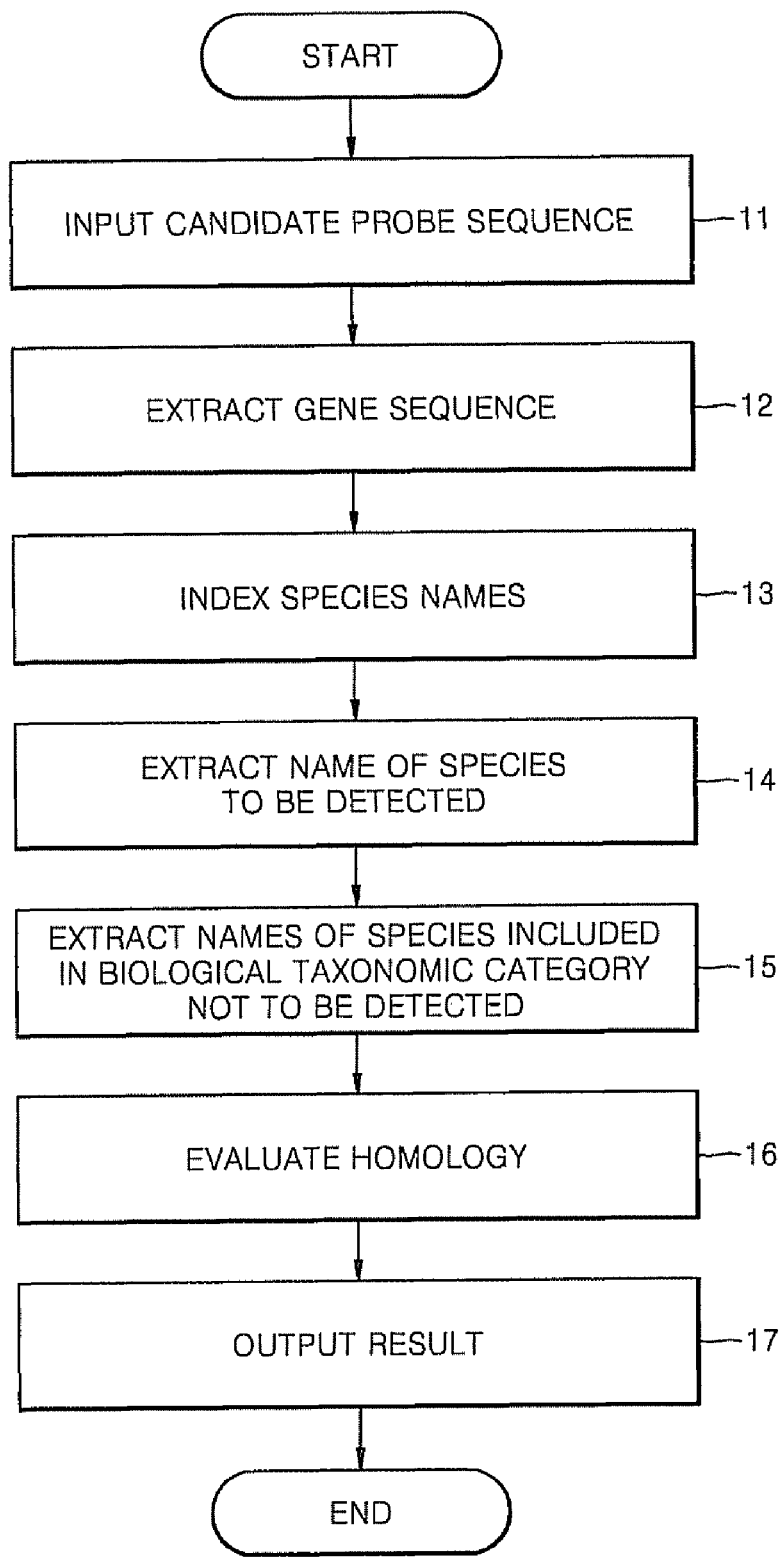
FIG. 1 is a flow chart illustrating an exemplary embodiment of a method for determining specificity of a candidate probe according to the present invention.

FIG. 1 is a flow chart illustrating an exemplary embodiment of a method for determining specificity of a candidate probe according to the present invention;

Referring to FIG. 1, the sequence of a candidate probe is input by a user (operation 11). More specifically, the user inputs the sequence of the candidate probe, the name of a species to be detected by the candidate probe, and the name of a biological taxonomic category to not be detected by the candidate probe.

The candidate probe sequence can be selected using any method. Additionally, any methods of selecting a probe sequence can be used in combination.

The sequence of a candidate probe can be input as exact nucleotide bases, such as A, C, G and T. Alternatively, a candidate probe sequence can be input using symbols representing variable nucleotide bases. The symbols for variable nucleotide bases represent 2 or more possible nucleotide bases. For example, M is A or C, R is A or G, W is A or T, S is C or G, Y is C or T, K is G or T, V is A, C or G, H is A, C or T, D is A, G or T, B is C, G or T, and N is A, C, G or T.

For example, if AACTTYATGTCCATGGGNGC (SEQ ID NO:1) is input as the sequence of a candidate probe, the variable base nucleotides, Y and N, are appropriately interpreted and thus the next steps are conducted automatically.

The species to be detected by the candidate probe sequence refers to a species that should be detected specifically by the candidate probe.

The biological taxonomic category not to be detected by the candidate probe sequence, is a biological taxonomic category for which it is desirable that the selectivity of the candidate probe sequence is such that the biological taxonomic category not be detected by the candidate probe sequence. However, some or all of the members of that input biological taxonomic category might be detectable by the input candidate probe sequence. For example, the biological taxonomic category may be a species, genus, family, order, class, phylum, or kingdom. Furthermore, the biological taxonomic category may be a subspecies, species, super species, subgenus, genus, or super genus, etc. The biological taxonomic category is not particularly restricted to the above examples.

Then, a gene sequence is extracted from a gene sequence database which stores gene sequence related information. The extracted gene sequence comprises a sequence homologous with the sequence of the candidate probe (operation 12).

The extraction of the gene sequence from a gene sequence database can be conducted using any known sequence search tool. For example, the sequence search tool can be BLAST, FASTA, or a Smith-Waterman algorithm. Any of these sequence search tools can access a gene sequence database, for example, the gene sequence database maintained by any of the National Center for Biotechnology Information ("NCBI"), the Swiss Institute of Bioinformatics ("SIB"), or the European Bioinformatics Institute ("EBI").

The user can set criteria for the minimum level of similarity required to infer homology between the extracted gene sequence and the sequence of the candidate probe. For example, the homology can be a homology of 95% or above. Also, the homology can allow for a 1 gap- or 1 bp-variation. The allowance of a 1 gap variation between the homologous sequence of the extracted gene and the sequence of the candidate probe means that the homologous sequence can be 1 bp shorter or longer than the sequence of the candidate probe due to the omission or insertion of one base. Also, the allowance of a 1 bp variation between the homologous sequence of the extracted gene and the sequence of the candidate probe means that the homologous sequence can have one different base from the sequence of the candidate probe.

The extracted gene sequence can also include information related to the gene sequence, for example, the name of the species from which the gene sequence was determined.

Then, the names of the species including the extracted genes are identified using information regarding the genes extracted from a taxonomy database which stores biological taxonomic information and gene sequence information (operation 13). The identification of the species including the extracted genes from the taxonomy database can be performed using any known sequence search tool to compare an extracted gene sequence with gene sequences in the taxonomy database to identify species with homologous sequences.

FIG. 2 is a table illustrating the contents of an exemplary embodiment of a taxonomy database according to the present invention.

Referring to FIG. 2, various organisms are classified according to a taxonomy system. For example, bacteria are classified into one of 845 possible higher taxa, 1502 possible genus, 19928 possible species, and 2228 possible lower taxa.

Then, the names of the species to be detected by the input candidate probe is extracted, if present, from the identified names of the species (operation 14).

The names of the species included in the biological taxonomy category not to be detected by the candidate probe sequence are extracted from the identified names of the species using the phylogenetic tree database, which stores phylogenetic tree information (operation 15). The species are included in the biological taxonomic category not to be detected. The phylogenetic tree database stores biological taxonomy classes and information of species belonging to each class. Thus, if a specific biological taxonomy class is known, information of species belonging to the class can be determined using the phylogenetic tree database.

Figure 3:
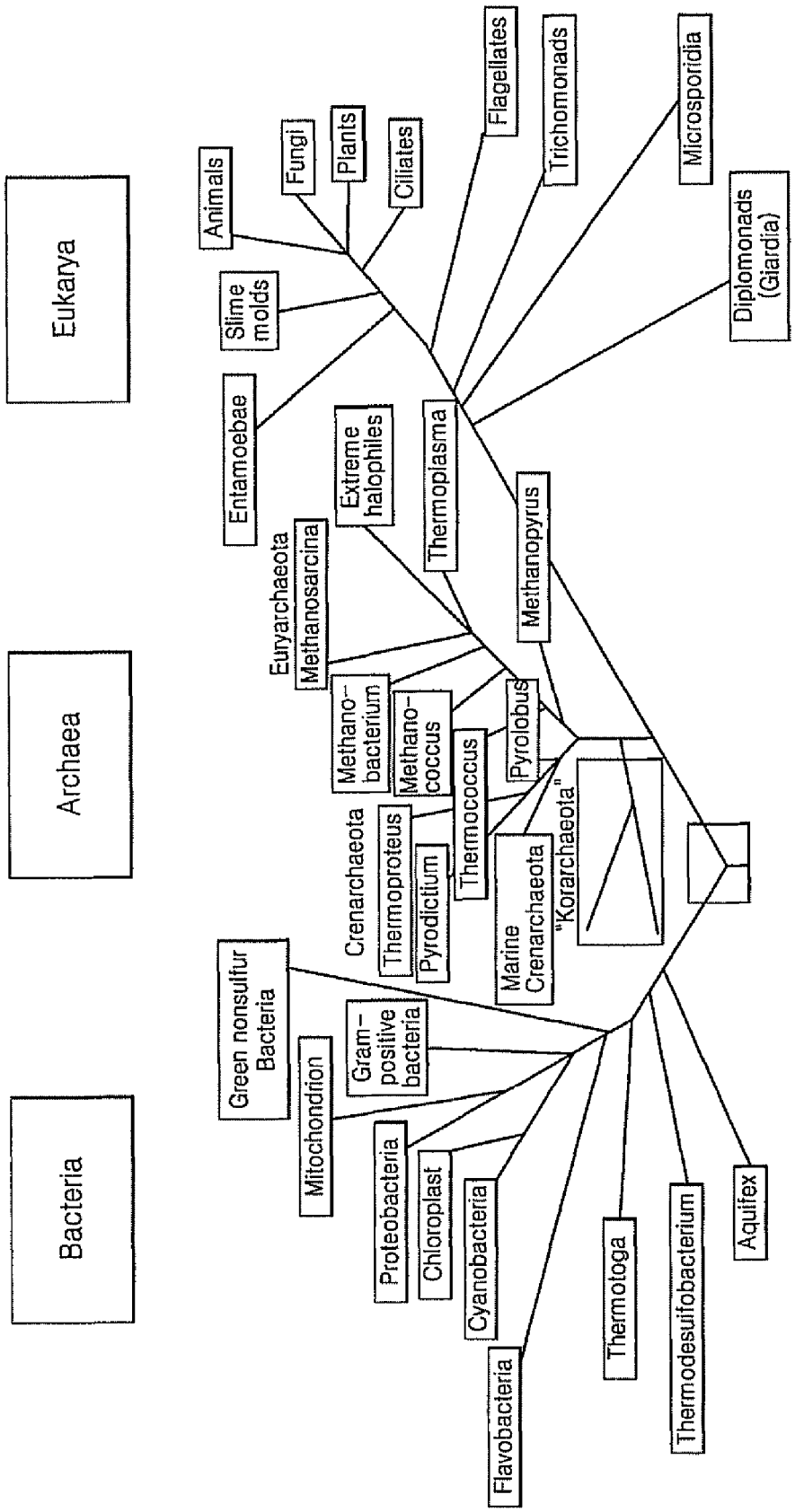
FIG. 3 is a schematic diagram of the structure of a universal phylogenetic tree, obtained by comparing ribosomal RNA sequences, and stored in an exemplary embodiment of a phylogenetic tree database according to the present invention.

FIG. 3 is a schematic diagram of the structure of a universal phylogenetic tree, obtained by comparing ribosomal RNA sequences, and stored in an exemplary embodiment of a phylogenetic tree database according to the present invention. In FIG. 3, each domain includes only a few main individuals or systems.

Figure 4:
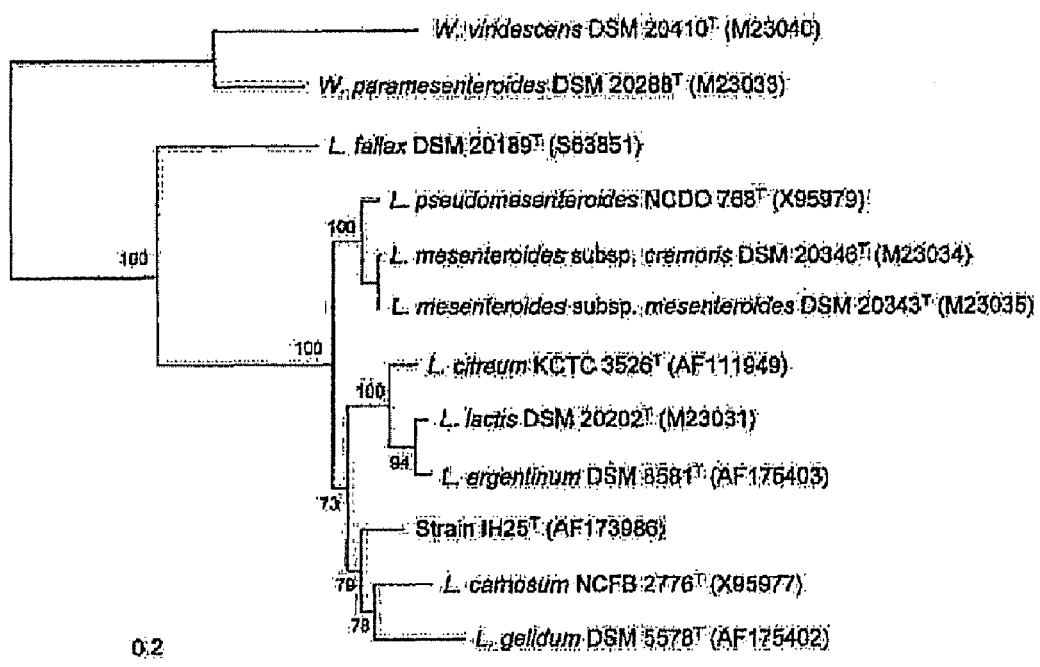
FIG. 4 is a schematic diagram of the structure of a phylogenetic tree for *Leuconostoc*, obtained by comparing the 16S rDNA sequence of each *Leuconostoc*, and stored in an exemplary embodiment of a phylogenetic tree database according to the present invention.

FIG. 4 is a schematic diagram of the structure of an exemplary embodiment of a phylogenetic tree for *Leuconostoc* obtained by comparing the 16S rDNA sequences of each *Leuconostoc* stored in the phylogenetic tree database.

A homology between the homologous sequences included in the genes of extracted species and the sequences of the candidate probe is scored or graded to evaluate the homology (operation 16). Scoring the homology is expressing the degree of homology between the candidate probe and each homologous sequence, for example 100%, 90%, or 70% homology between the two sequences. Grading the homology is to rank the homologous sequences by increasing degree of homology with the candidate probe.

Then, the names of the species to be detected by the candidate probe derived from the extracted gene sequences, the names of the species included in the biological taxonomic category not to be detected by the candidate probe derived from the extracted gene sequences, and results of the homology evaluation are output (operation 17).

In an exemplary embodiment of the present invention, a candidate probe for detecting an antibiotic-resistant form of tubercle bacillus disclosed in Korea patent laid-open No. 10-2005-0009052 is selected for input to the method. That is, the sequence cagccagctgagccaattca (SEQ ID NO:2) is input as the sequence of the candidate probe. Additionally, *Mycobacterium tuberculosis* and bacteria are input as the name of the species to be detected by the candidate probe and as the name of the biological taxonomic category not to be detected by the candidate probe, respectively.

As a result, *Mycobacterium tuberculosis* is output as the name of the species to be detected by the candidate probe and *Mycobacterium tuberculosis* and *Mycobacterium bovis* are output as the name of the species included in the biological taxonomic category not to be detected by the candidate probe.

Experimental results indicate that, when using the above candidate probe, *Mycobacterium tuberculosis* can be detected but *Mycobacterium bovis* can also detected at the same time. If the above two bacteria are clinically different but are regarded as substantially similar when detecting tubercle bacillus, distinguishing between the two bacteria is not necessary, and microarrays can be prepared using the candidate probe. However, if the two bacteria need to be distinguished, this candidate probe should not be used.

Figure 5:
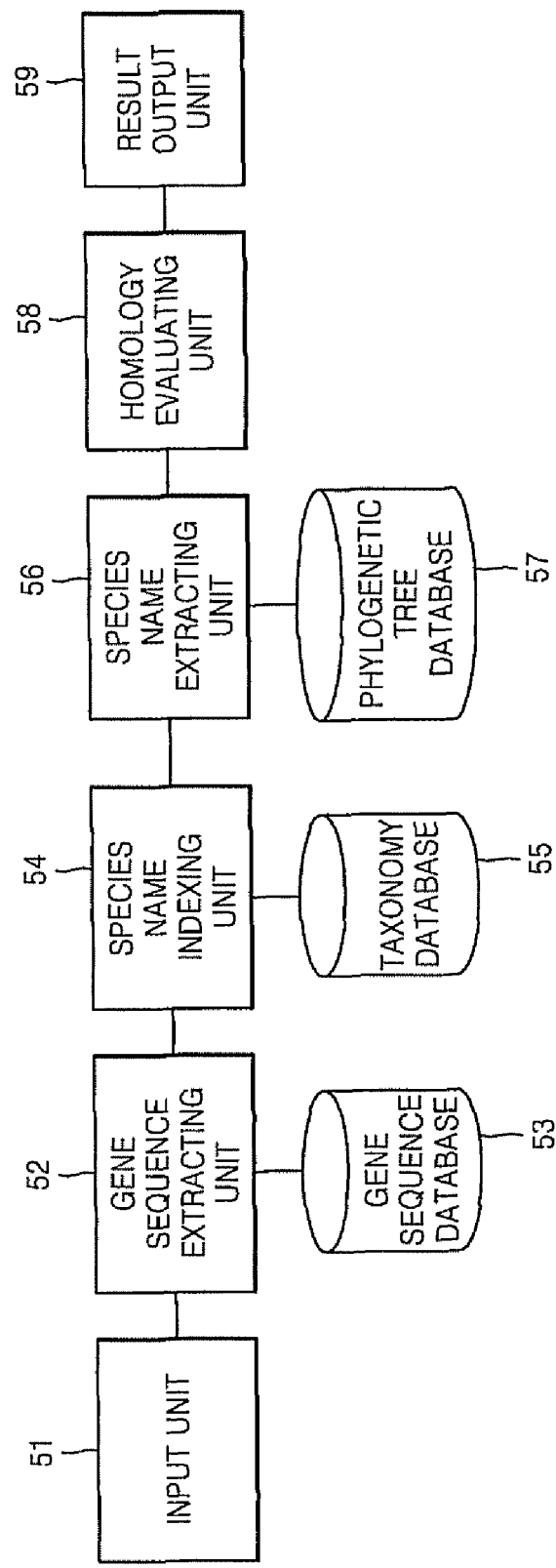
FIG. 5 is a block diagram of an exemplary embodiment of an apparatus for determining specificity of a candidate probe according to the present invention.

FIG. 5 is a block diagram of an exemplary embodiment of an apparatus for determining the specificity of a candidate probe according to the present invention.

Referring to FIG. 5, the apparatus comprises an input unit 51, a gene sequence extracting unit 52, a gene sequence database 53, a species name indexing unit 54, a taxonomy database 55, a species name extracting unit 56, a phylogenetic tree database 57, a homology evaluating unit 58, and a result output unit 59.

The sequence of the candidate probe, the name of the species to be detected by the candidate probe, and the name of the biological taxonomic category not to be detected by the candidate probes are input to the input unit 51.

The gene sequence comprising a sequence having a homology with the sequence of the candidate probe is extracted by the gene sequence extracting unit 52 from the gene sequence database 53, which stores gene sequence and, optionally, related information. The gene sequence database 53 can be, for example a gene sequence database provided by NCBI, SIB or EBI. The gene sequence database can also include information such as the name of the species comprising the extracted gene sequence.

In an embodiment of the present invention, the gene sequence extracting unit 52 can be a unit implementing a sequence searching tool such as BLAST, FASTA or a Smith-Waterman algorithm.

The user can set criteria for the degree of homology used by the gene sequence extracting unit 52, as described previously.

The names of the species including the extracted genes are identified in the species name indexing unit 54 using information regarding the extracted gene sequences extracted from the taxonomy database 55, which stores biological taxonomic and sequence information.

FIG. 2 is a table illustrating the contents of an exemplary embodiment of a taxonomy database 55.

The species name extracting unit 56 extracts the names of the species to be detected by the input candidate probe sequence from the identified names of the species, and the names of the species not to be detected by the input candidate probes from the names of the species identified using the phylogenetic tree database 57, which stores phylogenetic tree information.

FIG. 3 is a schematic diagram of the structure of a universal phylogenetic tree obtained by comparing ribosomal RNA sequences stored in an exemplary embodiment of a phylogenetic tree database 57.

FIG. 4 is a schematic diagram of the structure of an exemplary embodiment of a phylogenetic tree for *Leuconostoc* obtained by comparing the 16S rDNA sequences of each *Leuconostoc* stored in the phylogenetic tree database 57.

The homology evaluating unit 58 scores or grades a homology between the homologous sequences included in the genes of extracted species and the sequence of the candidate probe to evaluate the homology.

The result output unit 59 outputs the names of the species to be detected by the candidate probe derived from the extracted gene sequences, the names of the species included in the biological taxonomic category not to be detected by the candidate probe derived from the extracted gene sequences, and the result of the homology evaluation.

The invention can also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices. Such computer readable recording media can be accessed through the Internet. The computer readable recording medium can also be distributed over network coupled computer systems so that the computer readable code is stored and executed in a distributed fashion.

As described above, according to the present invention, the specificity and selectivity of a candidate probe sequence for detection of a desired target pathogen can be determined. In addition, the possible detection by the candidate probe of non-target pathogens, within all biospecies or in the range of biological taxonomic categories set by a user, can be identified by the method. Also, the specificity of a candidate probe can be verified using a continuously updated nucleic acid sequence or species taxonomic system database.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for determining specificity of a candidate probe sequence, wherein the method is executed on a specifically-programmed computer system, comprising:

inputting a candidate probe sequence, a name of a species to be detected by the candidate probe sequence, and a name of a biological taxonomic category;

extracting gene sequences from a gene sequence database, wherein the gene sequence database comprises gene sequence related information, wherein each extracted gene sequence comprises a sequence homologous with the candidate probe sequence;

identifying a name of a species corresponding to each extracted gene sequence using a taxonomy database, wherein the taxonomy database comprises biological taxonomic information and gene sequence information;

extracting, from among the identified names, the input name of the species to be detected if present;

extracting, from among the identified names, names for each species included in the input biological taxonomic category;

for each extracted species name, evaluating a degree of homology between the sequence in its extracted gene sequence homologous to the candidate probe sequence;

outputting the extracted name of the species to be detected if present, the extracted names for each species included in the input biological taxonomic category, and the degree of homology for each extracted species name; and then:

selecting the candidate probe sequence as a probe sequence for the input species to be detected if the input name of the species to be detected is output and the outputted names for each species included in the input biological taxonomic category does not include the names of species other than the input species to be detected;

discarding the candidate probe sequence as a probe sequence for the input species to be detected if the input name of the species to be detected is output but the outputted names for each species included in the input biological taxonomic category includes the names of species other than the input species to be detected; or selecting the candidate probe sequence as a probe sequence if the input name of the species to be detected is output, the outputted names for each species included in the biological taxonomic category includes names of species other than the input species to be detected, and it is unnecessary to distinguish between the input species to be detected and the outputted names for each species included in the biological taxonomic category.

2. The method of claim 1, wherein the biological taxonomic category is at least one category selected from the group consisting of a species, a genus, a family, an order, a class, a phylum, and a kingdom.

3. The method of claim 1, wherein homology between the candidate probe sequence and the homologous sequence of the extracted gene is 95% or greater.

4. The method of claim 1, wherein a 1 gap-variation or a 1 by variation is allowed in the homology between the candidate probe sequence and the homologous sequence of the extracted gene.

5. The method of claim 1, wherein the gene sequence related information comprises a name of a species from which the extracted gene sequence was obtained.

6. The method of claims 1, wherein inputting a sequence of the candidate probe comprises inputting ordered nucleotide bases.

7. A computer system for determining specificity of a candidate probe sequence, comprising:

a computer specifically programmed to include a gene sequence extracting unit, for extracting a gene sequence from a gene sequence database, wherein the extracted gene sequence comprises a sequence with homology to a candidate probe sequence;

a species name indexing unit, for indexing a name of a species corresponding to the extracted gene sequence using information regarding the extracted gene sequence extracted from a taxonomy database;

a species name extracting unit, for extracting a name of a species to be detected by the candidate probe sequence from the indexed names of species, and names of species included in a biological taxonomic category from the names of species indexed using a phylogenetic tree database; and a homology evaluating unit, for evaluating a homology between the sequence with homology to the candidate probe sequence contained in the extracted gene sequence and the candidate probe sequence.

8. The computer system of claim 7, wherein the biological taxonomic category is at least one category selected from the group consisting of a species, a genus, a family, an order, a class, a phylum, and a kingdom.

9. The computer system of claim 7, wherein the homology between the homologous sequence of an extracted gene and the candidate probe sequence is 95% or greater.

10. The computer system of claim 7, wherein a 1 gap-variation or a 1 by variation is allowed in the homology.

11. The computer system of claim 7, wherein the gene sequence database further comprises gene information comprising a name of a species from which a gene sequence is obtained.

12. The computer system of claim 7, further comprising an input unit, for inputting a candidate probe sequence, the name of a species to be detected by the candidate probe sequence, and the name of a biological taxonomic category.

13. The computer system of claim 12, wherein the input sequence is input as ordered nucleotide bases.

14. The computer system of claim 7, further comprising an output unit, for outputting an extracted name of a species to be detected, an extracted name of each species included in the biological taxonomic category, and results of the homology evaluation for each outputted species name.

15. A computer readable storage medium having recorded thereon a program for executing the method according to claim 1.

* * * * *